(12) United States Patent
Harris et al.

(10) Patent No.: US 8,073,234 B2
(45) Date of Patent: Dec. 6, 2011

(54) METHOD AND APPARATUS FOR INSPECTING OBJECTS USING MULTIPLE IMAGES HAVING VARYING OPTICAL PROPERTIES

(75) Inventors: Kevin M. Harris, New Bedford, MA (US); Paul A. Furze, Tiverton, RI (US)

(73) Assignee: Acushnet Company, Fairhaven, MA (US)

( * ) Notice: Subject to any disclaimer, the term of this patent is extended or adjusted under 35 U.S.C. 154(b) by 1135 days.

(21) Appl. No.: 11/845,177

(22) Filed: Aug. 27, 2007

(65) Prior Publication Data

US 2009/0060315 A1     Mar. 5, 2009

(51) Int. Cl.
*G06K 9/00* (2006.01)
(52) U.S. Cl. .................................................. 382/141
(58) Field of Classification Search .................. None
See application file for complete search history.

(56) References Cited

U.S. PATENT DOCUMENTS

| | | | |
|---|---|---|---|
| 4,355,331 A * | 10/1982 | Georges et al. | 378/98.11 |
| 5,777,244 A | 7/1998 | Kumagai et al. | |
| 5,912,942 A | 6/1999 | Schick et al. | |
| 5,960,098 A | 9/1999 | Tao | |
| 6,271,520 B1 * | 8/2001 | Tao et al. | 250/330 |
| 6,462,812 B1 | 10/2002 | Heene et al. | |
| 6,630,998 B1 | 10/2003 | Welchman et al. | |
| 6,891,672 B2 | 5/2005 | Whitehead et al. | |
| 6,928,140 B2 | 8/2005 | Furze | |
| 7,147,246 B2 * | 12/2006 | Breed et al. | 280/735 |
| 2001/0012389 A1 | 8/2001 | Welchman et al. | |
| 2003/0114754 A1 * | 6/2003 | Knoblich | 600/437 |
| 2004/0051790 A1 * | 3/2004 | Tamaru et al. | 348/223.1 |
| 2005/0276907 A1 | 12/2005 | Harris et al. | |
| 2006/0004292 A1 * | 1/2006 | Beylin | 600/476 |
| 2006/0071254 A1 | 4/2006 | Rhodes | |
| 2007/0035653 A1 | 2/2007 | Hong et al. | |

FOREIGN PATENT DOCUMENTS

JP     2002290707 A  * 10/2002

OTHER PUBLICATIONS

B06-41.2, Method and Apparatus for Inspecting Objects Using Multiple Images Having Varying Optical Properties, Kevin M. Harris, et al.

* cited by examiner

*Primary Examiner* — Daniel Mariam
*Assistant Examiner* — Elisa Rice
(74) *Attorney, Agent, or Firm* — Daniel W. Sullivan

(57) ABSTRACT

An automated object inspection system is presented. The inspection system includes an imaging system to produce at least two images of said object having different optical properties and an analyzer coupled to the imaging system to receive the images and to perform a variety of inspection operations on said images. The imaging system may produce images of the object under inspection in the visible range having varying exposure values. A vision engine included in the analyzer may combine said images through an algorithmic process into one image having high light dynamic range. Alternatively, the imaging system may produce images of the object in the visible or non-visible electromagnetic range. The analyzer may perform inspection routines on said images. An imaging system capable of producing digital video is presented, wherein each frame of video produced by said camera is composed of multiple images having different optical properties.

19 Claims, 5 Drawing Sheets

METHOD AND APPARATUS FOR INSPECTING OBJECTS USING MULTIPLE IMAGES HAVING VARYING OPTICAL PROPERTIES

FIELD OF THE INVENTION

This invention generally relates to a method and apparatus for inspecting objects, and more specifically to a method and apparatus for inspecting golf balls that utilizes multiple images having different optical properties.

BACKGROUND OF THE INVENTION

The manufacture of golf balls typically involves a series of sequential processes performed at different processing stations, typically spatially separated one from another. Golf balls typically have at least a core and a dimpled cover formed over the core. The outer cover of the golf ball is formed with various materials, such as urethane elastomers, balata, ionomers or any other appropriate materials. The cover surfaces are formed with dimples of various numbers, sizes and patterns, which improve flight distance, control and stability. The golf ball cover generally contains a white or other colored concentrate, or is painted. The outer surface of the ball covers usually have the manufacturers indicia printed thereon, as well as an application of a paint or clear coat for the purposes not only of good appearance but also of improving flight distance and protecting of the indicia.

Freshly coated golf balls are transported from a clear coat spray paint booth to a separate drying station at a remote location. Additional printing, such as a logo, may be applied over the cured clear coat.

Each process must be carefully monitored for quality assurance purposes. Inspections based on predetermined control criteria are performed to achieve a desired production quality. The manufacturer can manually inspect the entire lot if a given number of defective balls are found therein. Moreover, if a defect, such as a gross cosmetic defect or a defect affecting performance or durability, is found, the manufacturer may choose to shut down the entire system.

Since automated production is faster, each of the above processes can be performed at a separate automated processing station functioning at optimal efficiency and speed, so that the overall production rate is maintained at the desired high level. For instance, pad-printing apparatus preferably includes an array of print-pads arranged to apply a production print sequentially on various locations on the surface of the golf ball, with the golf ball being indexed before being passed to the next print-pad. Also, the clear coating process preferably is performed by an automated spray painting technique utilizing a spray paint booth with one or more spray paint guns. A quick drying clear coat paint having a catalyzing agent may be used to reduce the usual clear coat drying time of about ten hours to about one hour or less.

On the other hand, automation of the manufacturing process can cause various manufacturing defects. For example, automated pad-printing equipment may leave smudges from excess ink carried by the printing pad. Vibration or improper set-up, such as improper positioning or accidental switching of the paint supply hoses cutting off paint supply to the spray guns, causes defective coating on golf balls. Moreover, the clear coat paint may periodically clog the spray booth filter, interfering with proper spraying of paint.

While clear coat spray painting operation utilizing catalyzation can significantly reduce the curing time, catalyzation can also occur in the spray booth, resulting in a thick brittle coating on the spray booth filter and increasing the probability of spray paint malfunctions. Clogging of spray guns and gelling of the clear coat during application result in inadequate clear coating of the golf ball. Moreover, transferring the freshly coated golf ball to the curing station before inspection does not alert the operator to attend to unacceptable spray painting apparatus conditions until the end of the curing process. Thus, to maintain high production rates, it is necessary to identify the defective products early on in the treatment process.

Given the quality control necessary to meet production standards and the high production rates of golf ball manufacturing plants, actions to correct a malfunction in the automated processing equipment should be taken as soon as possible. Accordingly, there is a need for speedy and efficient inspection of golf balls so that any manufacturing problem may be corrected early to reduce further production of defective balls.

A variety of automated inspection systems and quality control methods are used in automated processing stations, such as coating, finishing, or otherwise affecting the surface appearance of products. Most of the known automated inspection systems employ vision cameras to capture an image of the products. The products to be inspected are typically illuminated to allow the cameras to see the entire products, e.g., dimpled golf balls are illuminated to prevent shadows from forming in the dimples. For example, commonly-owned U.S. App. No. 2001/0012389 discloses another golf ball inspection system using a custom lighting system. U.S. Pat. No. 5,777,244 discloses an elaborate system to illuminate golf balls. U.S. Pat. No. 6,462,812 discloses an inspection system utilizing a plurality of charge-coupled device (CCD) cameras to inspect indicia on golf balls. U.S. Pat. No. 5,960,098 discloses a vision system for inspecting fruits. This system also utilizes CCD cameras, albeit with an infrared lens, to capture the images of fruits.

At least one vision inspection system employs infrared cameras for inspection. U.S. Pat. No. 6,271,520 discloses a system for inspecting fruits. This system uses a first camera in the near infrared range and a second camera in the mid infrared range to capture images of the products to be inspected. The background information is removed and the two images are subtracted leaving the defects. A drawback of this system is that at least a portion of the exterior surface of the products to be inspected must be raised about 5° C. to 15° C. higher.

Commonly-owned U.S. Pat. No. 6,630,998 discloses light-emitting diodes mounted over the golf balls to be inspected to provide constant and even light sources. In addition to using non-ambient light sources for even lighting, the '998 patent discloses the use of ultraviolet lighting in order to detect the presence of a substance, such as a coating, applied to the surface of a golf ball. Images of the golf ball are captured by a detecting apparatus and then analyzed using discrete element detecting algorithm and industry standard blob analysis. Standard blob analysis tools count the number of discrete elements in the viewing area. This technique uses an algorithm to create a boundary outline around each discrete element being inspected. The boundary is broken down, such as into small line segments and arcs, to create a geometric representation which may be modified based on a best fit algorithm to match the object being inspected to a reference image. The algorithm then searches for breaks or significant changes in contour along the boundary, missing ink inside each boundary, and excess ink, marks, smudges, or doctor blade marks outside each boundary. Additionally, the boundary detection algorithm may calculate the relative positions of pairs of indicia, such as a logo and a number, to assure correct positioning. This is done by comparing the pattern detected in an inspection image with a predefined reference pattern. In a vision inspection system, the discrete element typically is identified as a continuous area of dark pixels exceeding a specified gray scale value without a break.

Cameras capturing images from the visible range in systems of the prior art generally produce images with low dynamic range, defined as the ratio of intensity of the highest luminance areas of a scene to the intensity of the lowest luminance areas of a scene. An inspection system employing low dynamic range image processing to capture an indoor scene may produce images that have low contrast, for instance a contrast of 50:1 or 100:1, while the scene in reality may display a contrast of 1,000:1 or more. Because the image sensors of the prior art systems can accommodate only a relatively small range of incident light, fine details on the surface of the object under inspection can be obscured or lost when the image is displayed. The poor light dynamic range of the images of the prior art inspection systems can make it difficult for the operators of the systems to discern certain defects on the surface of golf balls. For instance, minute but significant inconsistencies in coating coverage or small smears of indicia may not be scrutable in the image produced by the cameras of a prior art system by an inspection technician. In the event that the analyzer of the inspection apparatus detects a defect, subsequent scrutiny of the image by the human operator may fail to pick up said defect, leading the operator to allow the defective product to proceed to distribution.

Further, prior art inspection systems that employ image sensors in the non-visible electromagnetic range alone produce images that have limited optical properties. Defects that do not radiate the appropriate energy at the proper intensity (i.e., infrared, ultraviolet) cannot be detected by the sensors of these systems. There exists a need in the art for an inspection system that utilizes multiple images of the object under inspection having different optical properties so that wider range of defects can be detected and scrutinized without the need for complex lighting.

SUMMARY OF THE INVENTION

In accordance with the present invention, an automated object inspection system is presented. The inspection system comprises an imaging system to capture images of the object under inspection, and an analyzer to receive said images and to perform inspection routines on said images. The imaging system of the present invention comprises a detector to collect multiple images of the object under inspection, each image having different optical properties. In one embodiment of the present invention, the detector produces at least two, and preferably at least three, images of the object in the visible electromagnetic range using a low dynamic range digital image sensor, each image having a different exposure value to capture different ranges of incident light. A first image is exposed for a short amount of time to capture the brightest or most reflective areas of the scene in detail while leaving less bright areas in shadow in the resultant image. A second image is exposed for a moderate length of time to capture areas of the scene that are moderately bright or reflective in detail. A third image is exposed for the longest amount of time to capture dark or shadowed areas of the scene in detail. A vision engine of the analyzer then combines the separate images into one image that shows nearly all areas of the scene in detail. Areas that would appear either washed out or in shadow in the separate images are exposed correctly in the combined image, providing said image with a high light dynamic range. The vision engine compares said high dynamic range image with an exemplary image to analyze the object under inspection for surface defects or inconsistencies.

Another embodiment of the present invention presents an inspection system arranged as in the previous embodiment. The imaging system, however, employs a high dynamic range digital image sensor to collect images of the object under inspection. The detector of the present embodiment collects at least two images of the object, varying the exposure value for each image. The images are blended at the vision engine to produce an image having a high light dynamic range.

In another embodiment of the present invention, the imaging system comprises a camera having at least two photosensitive pixel arrays (e.g., CCD or CMOS devices) wherein each pixel array—through the use of neutral density filters or electronic apertures working in conjunction with individual pixels—is light-transparent to a different degree. The major advantage of the multi-chip camera of the present invention is that it produces at least two images of the object under inspection after one snap of the shutter of the camera. Each image generated by a photo-pixel array of the present embodiment captures areas of the scene with particular luminance values. A vision engine combines the separate images into one image having a high light dynamic range and subsequently performs inspection routines on said image.

In yet another embodiment of the present invention, the imaging system comprises at least two image sensors, at least one of which being capable of capturing an image in the non-visible electromagnetic range. The vision engine receives detection signals from the imaging system and analyzes the images, which can be any combination of visible and non-visible electromagnetic range images, against an exemplary master image for surface and/or sub-surface defects. The vision engine may combine the images captured by the imaging system or leave them separate. Alternatively, both images can be in the non-visible range. A camera of the present embodiment configured to capture images in the visible range may produce high or low dynamic range images.

Another embodiment of the present invention presents a high dynamic range video imaging system used for surveillance purposes. In accordance with an aspect of the present invention, a video imaging system is comprised of an image detector having at least two photosensitive pixel arrays, similar to the multi-chip sensor discussed in previous embodiments. For each frame of video collected by an image sensor of the present invention, light is directed, through use of a beam-splitter or number of half-silvered mirrors, to three CCD or CMOS photosensor arrays. At least two arrays are overlaid with neutral density filters, each neutral density filter being light-transparent to a different degree. Each image generated by a pixel array of the three-chip camera captures areas of the scene with particular luminance values. When digitally combined, each frame of video has a high light dynamic range. The resulting video images offer improved visual detail, which can be useful when utilized in security cameras or video surveillance equipment.

In a final embodiment of the present invention, an imaging system comprises two digital video image sensors, each image sensor configured to produce digital video in different ranges of the electromagnetic spectrum. For example, a first digital video image sensor collects images in the visible range and a second image sensor collects images in the infrared range. Each frame of the video in the visible range corresponds to one frame of video in the infrared range.

The embodiments of the present invention can be used in manufacturing quality assurance applications, medical imaging and/or surveillance.

DETAILED DESCRIPTION OF THE INVENTION

Figure 1:
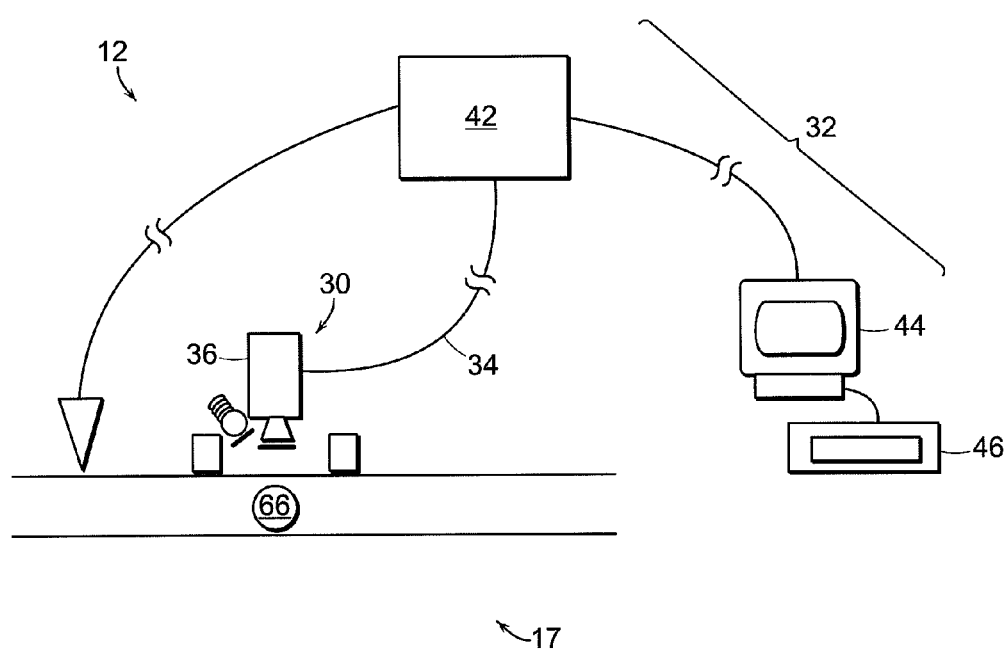
FIG. 1 is a schematic diagram of an automated processing station of the present invention comprising an imaging system 30 and an analyzer 32.

As illustrated in FIG. 1, the present invention relates to the modification of or addition to an automated object inspection system 12. One such inspection system using low dynamic range image processing is described in the '998 patent and is incorporated by reference herein in its entirety. Automated inspection system 12 permits continuous, objective inspection of all of the objects being processed by automated processing apparatuses without interrupting or slowing down or otherwise interfering with processing or production of the objects. As described in further detail below, the embodiments of the present invention help to refine the inspection process and hence increase the efficiency of production.

For illustrative purposes, a number of the embodiments of the present invention are discussed in regard to the inspection of golf balls; however, the principles of the present invention are not limited to golf balls and can be used with any manufactured items. Referring to FIG. 1, inspection system 12 comprises an imaging system 30 and an automated analyzer 32 linked via electronic link 34. Detector 36 of imaging system 30 views and detects golf ball 66 and provides a detection signal to automated analyzer 32.

In an embodiment of the present invention, detector 36 collects images via a conventional low dynamic range digital photosensor. The photosensor may be a charged-coupled device (CCD) or a complementary metal-oxide-semiconductor (CMOS). Further, detector 36 may be an area-scan camera or a line-scan camera as described in the '998 patent. Preferably, detector 36 collects multiple images of the object under inspection, each image having a different exposure value depending on the luminance of the scene. Those images are in turn combined at vision engine 42 to produce one image that offers a range of luminance contrast—and thus a range of visual detail—that spans the luminance range defined by the separate images, henceforth called a "high dynamic range." The visual detail of the combined image is subsequently greater than that of any single image captured by a conventional low dynamic range digital camera found in the inspection systems of the prior art.

Figure 3C:
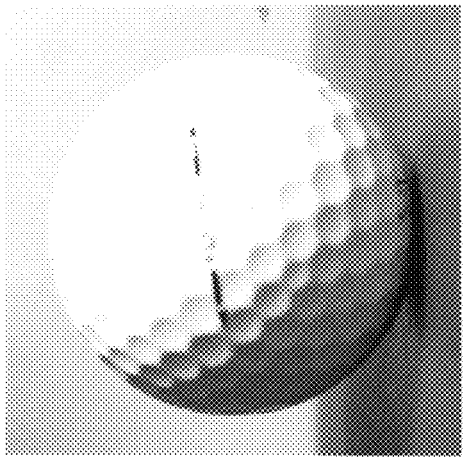
FIG. 3C shows an image of a golf ball taken with a long exposure.
Figure 3B:
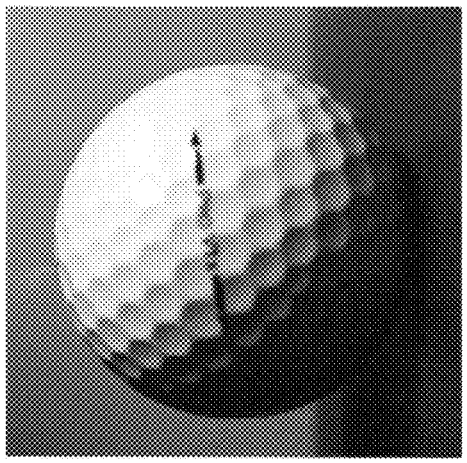
FIG. 3B shows an image of a golf ball taken with a mid-length exposure.

For example, detector 36 collects three images of golf ball 66 in rapid succession. Preferably, each image is identical with respect to perspective (i.e., the position of the camera with respect to the subject and the zoom of the lens) and white balance, but each image varies with respect to overall brightness, controlled by f-stop, exposure time, filtering or other means. Detector 36 can be calibrated to automatically expose each image for a different amount of time, according to the luminance of the scene. A light meter may be used in conjunction with detector 36 to evaluate the appropriate variation in number of f-stops for each image of golf ball 66. This process of creating three differently exposed images of golf ball 66 results in images that display great surface detail of different areas of golf ball 66. FIGS. 3A, 3B and 3C show examples of three images generated by detector 36 that vary with respect to number of f-stops. FIG. 3B shows an image of golf ball 66 taken with exposure that is considered neutral. The image is exposed to capture areas of moderate-intensity luminance. Hence, the most brightly lit area, the top right-side area, is over-exposed and washed out. The middle section of golf ball 66, the section that is moderately lit, is shown in detail, while the bottom left-side area, which receives little incident light, is shown in shadow. FIG. 3A shows an image of a golf ball taken with an exposure shorter than that of the neutral image, e.g., with an f-stop difference of −2. The area of the golf ball that is most brightly lit by the lighting apparatus of the inspection system, the top right-side area, is shown in great detail in the image of FIG. 3A, while rest of the golf ball, the areas that constitute the darker parts of the scene, remains in shadow. FIG. 3C shows an image of golf ball 66 taken with an exposure longer than that of the neutral image, e.g., with an f-stop difference of +2, which washes out the detail of the top right-side and middle section of the golf ball but shows the darkest part of the scene, the bottom left-side, in great detail. It should be noted that those of ordinary skill in the art will determine the appropriate number of f-stops or exposure times to achieve images with the proper luminance contrasts.

Figure 3D:
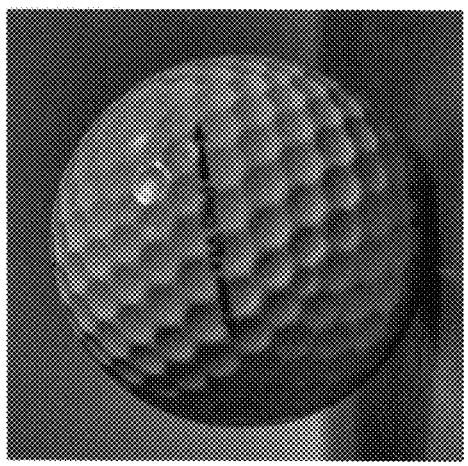
FIG. 3D shows an image of a golf ball created by digitally combining the three images of FIGS. 3A, 3B, and 3C to produce an image with a much greater light dynamic range.
Figure 3A:
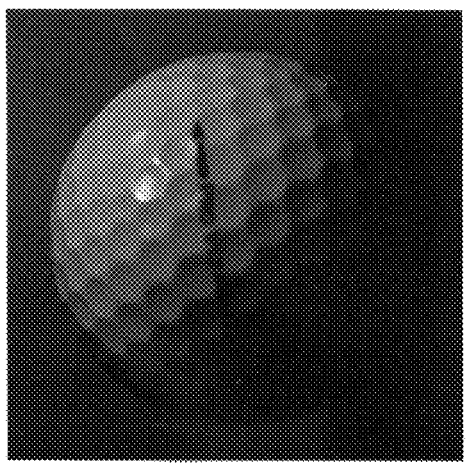
FIG. 3A shows an image of a golf ball taken with a short exposure.

FIG. 3D shows the digital combination of the images shown in FIGS. 3A, 3B and 3C. In accordance with the present invention, vision engine 42 may blend the images of golf ball 66 having varied exposure values, typically in the form of RAW data files, using an HDR imaging program such as Photomatix Pro, available by download at http://www.hdrsoft.com/order.html, from HDRsoft SARL, located in Montpellier, France, among other available programs. In the image of FIG. 3D, areas of golf ball 66 that were over-exposed or left in shadow in the separate images of FIGS. 3A, 3B and 3C are shown in nearly equal detail. Surface areas of golf ball 66 that would be obscured by bright light reflection in images created by low dynamic range image processing are visible in the high dynamic range image. Likewise, surface areas that would be obscured by shadows in low dynamic range images are visible in the high dynamic range image. In other embodiments of the present invention, discussed in greater detail below, detector 36 may generate images of golf ball 66 in both the visual and non-visual electromagnetic range to capture a greater range of surface and/or subsurface detail of golf ball 66.

The high dynamic range images generated by detector 36 and vision engine 42 of the present invention are evaluated by analyzer 32, which performs various analytical tasks, such as statistics processing, task scheduling, generation of reject signals or further control signals, and/or alarms. Analyzer 32 can also record the image of inspected golf ball 66 for future reference. Analyzer 32 may be placed near, and most preferably adjacent to, the operator to enable easy and quick access to both analyzer 32, to view a defect, and inspection station 17, to attend to and to correct the cause of the distortion. Analyzer 32 includes a high-speed vision engine 42, which has a computer processor, monitor 44 and keyboard 46, among other components. After performing exposure blending, vision engine 42 analyzes the high dynamic range image by comparing it to an ideal reference image.

Images of inspected golf ball 66 may be displayed on monitor 44, so that the operator may compare the images to an ideal image, particularly if golf ball 66 is defective. Discussed in more detail below, monitor 44 may be a high dynamic range display device; alternatively, analyzer 32 may include monitor 44, said monitor being a conventional display device, and vision engine 42, said vision engine performing a tone-mapping technique on high dynamic range images before sending them for display to monitor 44. The improved luminance contrast and visual detail of the displayed high dynamic range image can assist operators in discerning surface blemishes detected by analyzer 32, hence improving the filtering of defective products from the lot of golf balls undergoing inspection. The operator can readily confirm the defects detected by analyzer 32. Highlights and color error markers can be set to emphasize important features or problems in the image displayed on monitor 44. A freeze frame feature may be provided to freeze a defective ball on monitor 44 for closer scrutiny while inspection continues. Such a feature also permits the scanned image to be stored and displayed so that the operator may view the areas found defective by analyzer 32 while allowing the inspection process to continue. The frozen image remains displayed for an amount of time specified by the operator or until manually reset.

A variety of inspection routines may be performed by vision engine 42, such as finding the center of golf ball 66, checking overall dimensions and contours, inspecting for contamination, and/or determining various characteristics of a surface treatment, such as possible defects in the paint, clear coating or indicia/markings. The specific inspection routine performed on the golf ball is selected based on the process being inspected, as is described fully in the '998 patent.

As described above, in one embodiment of the present invention detector 36 is comprised of a charged-coupled device (CCD) or complementary metal-oxide-semiconductor (CMOS) sensor capable of capturing images of golf ball 66 in the visible electromagnetic range at various exposure values. In accordance with this embodiment, the sensor of detector 36 captures at least two images of golf ball 66 in short succession and from the same perspective. As shown in the image of FIG. 3A, one image may be taken with a short exposure so that the brightest parts of the scene are visible in the resultant image. One image may be taken with a mid-length exposure, as shown in FIG. 3B, to capture the area that is less brightly lit than the lightest areas and more brightly lit than the darkest areas in visible detail in the resultant image. One image may be taken with a long exposure, as shown in FIG. 3C, so that the darkest parts of the scene are visible in the resultant image.

Vision engine 42 then blends the images collected by detector 66 through the use of an exposure blending program, e.g., Photomatix Pro, into one image that offers visible detail of nearly all parts of the scene, light and dark. The imaging technique offered by programs such as Photomatix Pro uses an algorithmic process to combine the tonal and luminance details of images, most often in RAW data file format, but also in TIFF and JPEG format. The resultant images, known as high dynamic range images, have far greater light dynamic range than the singular images generated by conventional digital or film cameras. When said high dynamic range images are displayed, therefore, they provide an operator with more detailed images against which he can compare the results of the inspection routines performed by analyzer 32.

In another embodiment of the present invention, inspection system 12 produces high dynamic range images of objects under inspection through the use of a high dynamic range image sensor. For example, instead of the traditional 8-bit per pixel digital photosensor, detector 36 can comprise a 10-bit per pixel digital photosensor capable of capturing images in 1024 shades of gray and hence providing images with a luminance ratio of 1024:1. Alternatively, detector 36 can comprise a 12-bit per pixel digital photosensor capable of capturing images in 4096 shades of gray and with a luminance contrast of 4096:1. Detectors with higher bit per pixel count can be used to increase the luminance contrast ratio. In accordance with this embodiment of the present invention, the images produced by the high-dynamic range image sensors of detector 36 having the luminance ratios described above would display golf ball 66 in much greater detail and would more closely resemble the scene in reality than images produced by inspection systems of the prior art. Preferably, detector 36 captures at least two images of golf ball 66 at varying exposure values. The images are combined at vision engine 42 using the algorithmic blending process discussed above and utilized in previous embodiments. An example of an image produced according to this aspect of the invention is shown in FIG. 3D.

Also in accordance with the above embodiment, detector 36 can comprise a high electrical dynamic range image sensor capable of producing images with high luminance ratios. In typical low electrical dynamic range CCD or CMOS sensors in the vision inspection apparatuses of the prior art, the ratio of the largest non-saturating signal to the standard deviation of noise under non-illuminated conditions is small. When light hits the photoactive element of a pixel cell in the array of a sensor, photons are converted into electrical charge proportional to light intensity. The low electrical dynamic range sensors employed by vision systems of the prior art reach saturation in response to a much smaller intensity of incident light, resulting in images in which areas of the object under inspection that are highly reflective or brightly illuminated look only as bright as areas that reflect much less incident light. If photosensors collect more light than what is required to saturate a pixel, excess electrical charge can spill onto adjacent pixels, resulting in an effect called "blooming," and producing a bright spot on the image. Under these conditions, defects on the surface of the object can be obscured. Detector 36 may utilize any of the various types of high electrical dynamic range image sensors. One example of a high electrical dynamic range image sensor that may be included in detector 36 is described in U.S. Publ. Pat. App. No. 2006/0071254, incorporated by reference herein in its entirety. Each pixel of this CMOS sensor includes a transistor that is intentionally made to leak a small amount of electrical charge in order to lengthen the amount of time and increase the amount incident light required to saturate the photosensor. The sensor is able to collect a greater range of the incident light of the scene to produce images that in turn have a higher light dynamic range.

Another example of a high electrical dynamic range image sensor that may be used in detector 36 is taught in U.S. Publ. Pat. App. No. 2007/0035653, incorporated by reference herein in its entirety. In this example, the pixels of the photoarray are overlaid with neutral density filters having varied light-transparency values. Pixels coupled to neutral density filters that have greater transparency become saturated in response to a smaller amount of incident light. Pixels coupled to neutral density filters that are more opaque require a greater amount of incident light to reach saturation. The individual pixels of this array are light-sensitive to varying degrees, and so can capture the incident light of dark, moderately bright and very bright areas of the scene. Subsequently, the image generated by the information collected by the set of pixels has a greater light dynamic range than an image produced by a conventional digital photosensor.

Preferably, inspection analyzer 32 utilizes linear values to store image information that corresponds to the relative or absolute values of radiance or luminance of the scene. Preferably, inspection analyzer 32 utilizes 16-bit or 32-bit floating point numbers to represent the linear encoding to produce an image that more closely resembles the visible luminance of the scene.

In accordance with an aspect of the present invention, monitor 44 of analyzer 32 can be a high dynamic range display device. Such a device is described in U.S. Pat. No. 6,891,672 and is incorporated by reference herein in its entirety. Monitor 44 is more preferably a rear projection display having at least one light modulator. Preferably, at least one light modulator is a high resolution light modulator having a pixel array comprising at least 500 pixels in each direction, and more preferably comprising at least 1000 pixels in each direction. Unlike most conventional computer monitors which can reproduce an image luminance range of at-most 100:1—no matter the actual luminance range produced by an HDR photosensor or HDR exposure-blending technique— the monitor of the present embodiment is capable of displaying the full luminance contrast of the images produced in the processes described in the previous embodiments. Preferably, monitor 44 comprises a display that is capable of reproducing an image having a luminance contrast of 1000:1 or higher.

In accordance with another aspect of the present invention, monitor 44 comprises a conventional low dynamic range display device. Vision engine 42 employs a tone-mapping technique to convert the tonal values corresponding to the high light dynamic range of images produced by the processes explained in previous embodiments. This process allows the monitor to display a image that appears to have the high luminance contrast of the original HDR image, but that actually has tonal values that correspond to a lower dynamic range, one that is capable of being displayed on a low dynamic range monitor.

In another embodiment of the present invention, detector 36 comprises a camera with at least two photosensitive pixel arrays. For illustrative purposes, the present embodiment is discussed with regard to a camera utilizing at least two CCDs; however, detector 36 may utilize at least two CMOS devices instead. The incident light of the scene is split using a beam splitter apparatus or a number of half-silvered mirrors and is projected onto one of each of the CCDs of detector 36. Instead of the conventional use of RGB color filters over each of the CCDs, at least two of the CCDs of detector 36 are overlaid with neutral density filters. Preferably, each neutral density filter coupled to a CCD of detector 36 is light transparent to a different degree. The pixels of the array of each CCD will subsequently respond with varying sensitivity to the incident light of the scene, creating three monochrome images of varying exposure values. As in the first embodiment discussed above, the monochrome image produced by each of the CCDs will make visible a different area of the golf ball under inspection. If three CCDs are used, the area that is most brightly lit or most reflective will be shown in detail in the image produced by the CCD coupled to a neutral density filter that is the least light-transparent. The area of the golf ball that is moderately reflective or moderately lit will be shown in detail in the image generated by the CCD coupled to a neutral density filter that is more light transparent. Finally, the area of the golf ball that sits in shadow or that is least bright will be captured in the image produced by the CCD that either stands alone or is coupled to a neutral density filter that is most light-transparent. The three images captured by the three-chip camera of detector 36 will display detail that is typically washed out or otherwise obscured because of pixel saturation and poor brightness contrast in conventional digital photosensors.

In another example of this embodiment, detector 36 comprises a camera having at least two CCDs or at least two CMOS devices, wherein a beam splitter or a number of half-silvered mirrors direct light to each of the photosensitive pixel arrays. The individual pixels of each photosensitive pixel array are overlaid with a neutral density filter. Each pixel array is configured to be light transparent to a different degree. The images produced by at least one pixel array will show moderately bright or bright areas of the scene in detail. The images produced by at least another pixel array will show dark areas of the scene in detail.

Alternatively, detector 36 comprises a camera having at least two CCDs or at least two CMOS devices, wherein a beam splitter or a number of half-silvered mirrors direct light to each of the photosensitive pixel arrays. The individual pixels of each photosensitive pixel array work in conjunction with an individual electronic aperture in order to control the amount of light shone on each pixel. The aperture size of each pixel can be controlled by a software program. At least one pixel array is configured to produce images showing moderately bright or bright areas of the scene in detail. At least one pixel array is configured to produce images showing dark areas of the scene in detail.

The information encoded by each photosensitive pixel array is combined at vision engine 42 using an algorithmic photo-blending process as in previous embodiments to create one image that has a high dynamic range. Vision engine 42 will then perform quality assurance operations. The major advantage of this embodiment is that only one snap of the shutter of detector 36 is required. Detector 36 takes one picture of golf ball 66 to produce at least two images of the ball.

In yet another embodiment of the present invention, detector 36 uses multiple sensors to capture images of golf ball 66 in the visible and non-visible range sequentially or simultaneously. For example, detector 36 can comprise a CCD photosensor and an infrared sensor to collect images of golf ball 66 that provide data that could not be measured by a visible light camera or an infrared sensor alone. The use of infrared imaging in quality assurance operations is discussed in commonly-owned U.S. Publ. Pat. App. No. 2005/0276907, and is incorporated by reference herein in its entirety. Infrared imaging, also known as thermography, is a non-contact optical method where an accurate two-dimensional mapping of steady or transient thermal effects is constructed from the measurement of infrared energy emitted by the target. As discussed above, coating and paint materials can be applied unevenly to golf balls due to a variety of reasons, including catalyzation inside the spray booth filter and improper positioning of the golf ball on the spraying apparatus. After the paint or coating is applied, the solvents evaporate from the ball's surface by convection and create a cooling effect on the surface of the ball. This transient cooling causes the temperature on the surface of the ball to drop. In accordance to one aspect of the present invention, an infrared sensor can detect the unpainted or uncoated areas immediately after the paint or coating is applied to the ball. Coating defects, such as blistering and sub-surface corrosion spots, can be detected in infrared images as a result of the differences in the thermal diffusivity of the defective and non-defective areas. Often a fraction of a degree is adequate for reliable detection and identification of the thermal signature of the defect. The same technique can potentially be used for rapid assessment of the variations in the coating thickness. An acceptable infrared sensor/camera is the Thermovision® 570 commercially available from Agema Corp. Other suitable infrared sensors/ cameras include those available from Nikon (JP), Infrared Systems, Inc. (Reno, Nev.), Electrophysics, Infrared Solutions, Inc. (Plymouth, Minn.), among others.

The images captured by the sensors of detector 36 are sent to analyzer 32, where potential defects and inconsistencies on the surface of golf ball 66 are compared to master images of an exemplary golf ball. For instance, the image of golf ball 66 produced by the visible light CCD sensor can provide data related to the position and quality of application of indicia, while the infrared image can provide data related to the application of paints and other coating materials. Where infrared and visible range images are combined, the resultant image can show a pattern of thermal cooling on the surface of golf ball 66. In spots where no cooling occurs, this may be an indication that coating is absent or is too thin. If the application of indicia has already occurred, the darker pigment of the indicia may also radiate warmth that can distort the thermal cooling pattern shown in the infrared image. The visible range image combined with the infrared image could then provide analyzer 32 or the operator with the information necessary to distinguish coating application defects from areas where indicia are applied. In accordance with an aspect of the present invention, infrared and other non-visible range imaging can be combined with high dynamic range images, as discussed above, or conventional low dynamic range images.

The present embodiment is not limited to the collection of images in the visible and infrared range. Many combinations of at least two images with different electromagnetic properties may be used. A detector of the present invention can comprise, but is not limited to, ultraviolet and visible light sensors, ultraviolet and infrared sensors, multiple X-ray sensors, or X-ray and visible light sensors. For example, an ultraviolet radiation generating apparatus may be used in conjunction with a digital photosensor to produce image of a golf ball under inspection. A first image is produced to capture the fluorescence emitted from the clear coat applied to the cover of the golf ball after said golf ball is radiated with ultraviolet energy. A second image is produced to capture the look of the ball in the visible range. When overlaid or compared separately, inconsistencies in the pattern of fluorescence may indicate defects or blemishes in the clear coat.

Figure 2:
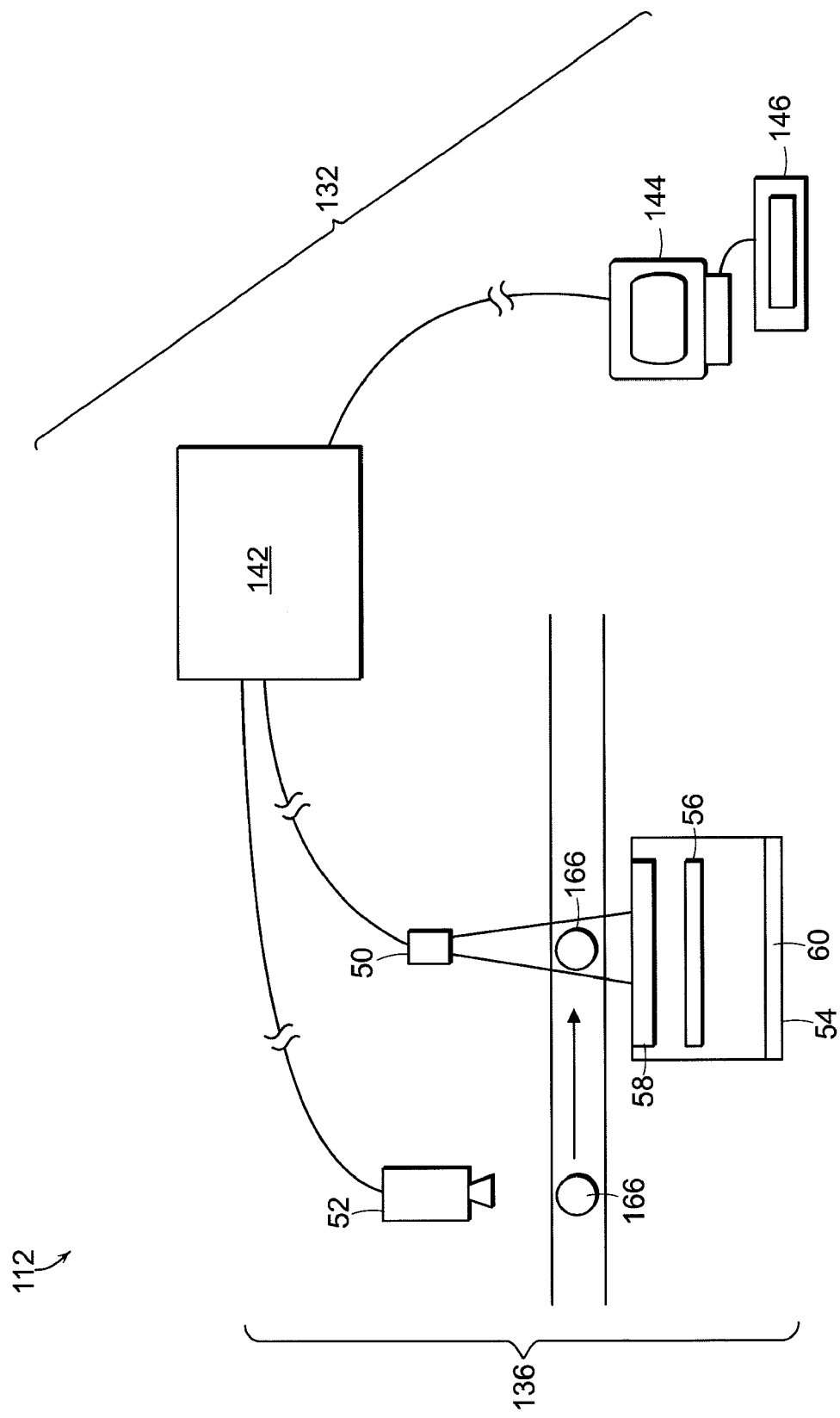
FIG. 2 is a schematic diagram of an automated processing station of the present invention comprising a detector 136, having both a visible electromagnetic range digital photosensor and an x-ray detector, and analyzer 132.

In accordance with this embodiment of the present invention and as illustrated in FIG. 2, automated inspection system 112 can comprise detection apparatus 136 comprised of solid-state CCD photosensor 52 and digital X-ray detection sensor 54. Solid-state CCD photosensor may be a high electrical dynamic range sensor or a conventional low dynamic range sensor. Detector 136 may include a digital X-ray detector as taught in U.S. Pat. No. 5,912,942, which is incorporated by reference herein in its entirety. In an example of the present embodiment, X-ray generating apparatus 50 emits radiation which is transmitted through golf ball 166 and onto detection sensor 54. Detection sensor 54 may include CCD or CMOS photosensor array 56 disposed between scintillator 58, comprised of gadolinium oxysulphate ($GD_2SO_2$) or thallium-doped cesium iodide (CsI(Tl)), and tungsten plate 60. X-ray radiation is converted into visible light by the scintillator; the photons emitted by the scintillator are in turn converted into electrical charge by the photosensor array, and the tungsten plate absorbs excess radiation. The X-ray image collected by detection sensor 54 is transmitted to vision engine 142 via an electronic link for quality control analysis. The image captured in the visible range by solid state CCD photosensor 52 is also processed at vision engine 142. The two digital images may be combined to produce one image that offers data relating to the surface and subsurface properties of golf ball 166. Alternatively, vision engine 142 may perform inspection operations on each image separately. Using X-ray and visible range images, analyzer 132 may inspect golf ball 166 for proper core position, core porosity, the existence of void(s) and cover or core layer concentricity. A visible range image can provide analyzer 132 with the proper boundaries of the golf ball, while an X-ray image can show the position of the core, core layers or cover layers in relation to the outer boundary of the ball as shown in the visible image. X-ray imaging used in conjunction with visible range imaging may also show bubbles under the surface of golf ball 166, or delamination of the sub-surface layers of golf ball 166, or contamination inside the ball. The visible range image can serve to show these major internal defects in relation to the outer boundary of golf ball 166.

Figure 4:
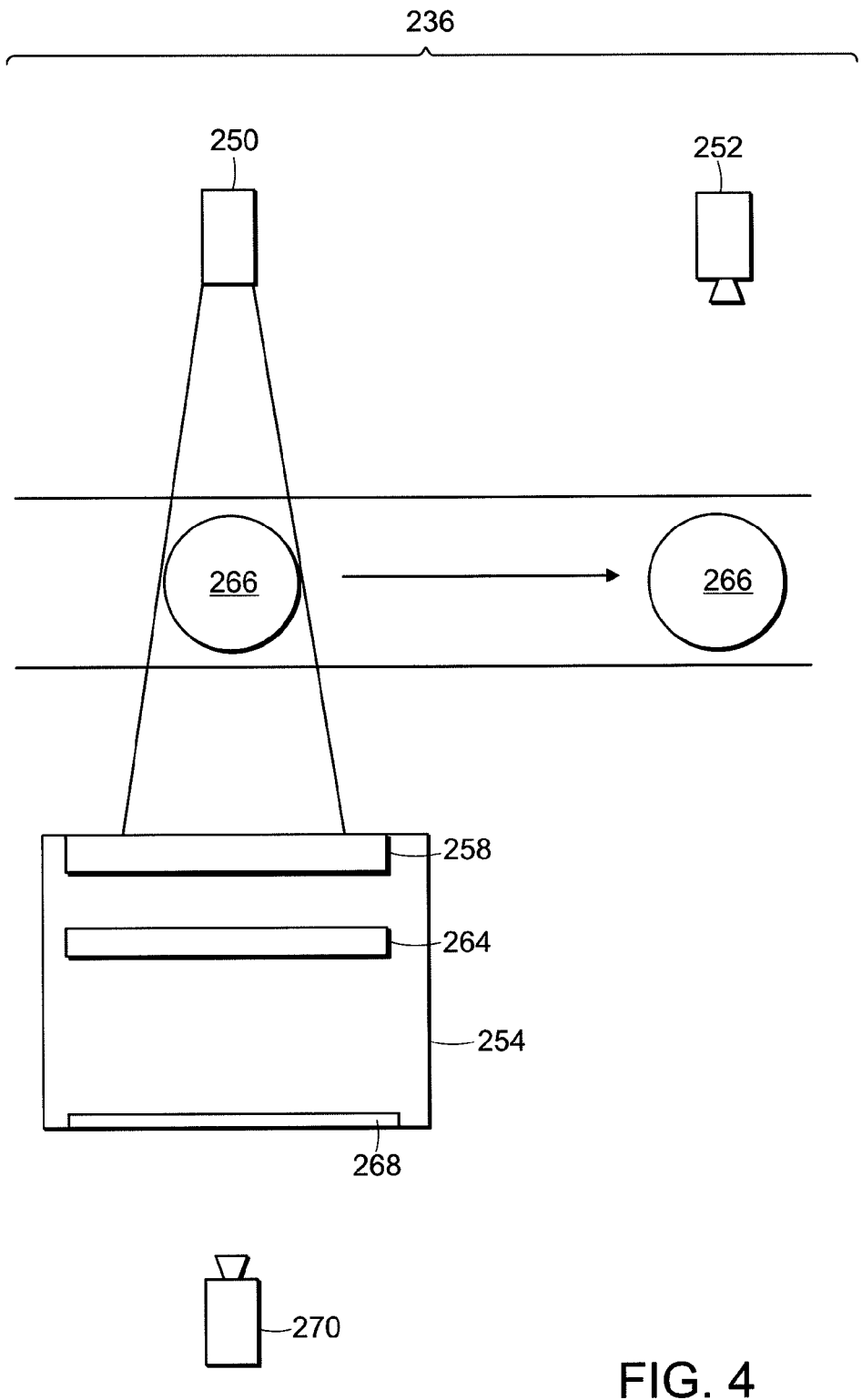
FIG. 4 is a schematic diagram of detector 236, including a visible electromagnetic range digital photosensor and an x-ray detector.

In another example of the embodiment discussed above, an inspection apparatus comprises an analyzer, including a vision engine, monitor and keyboard, connected via an electronic link to detector 236. Detector 236, shown in detail in FIG. 4, comprises x-ray generating apparatus 250, x-ray detector 254, digital photosensor 270 and digital photosensor 252. In accordance with this aspect of the present invention, x-ray generating apparatus 250 emits radiation which is transmitted through golf ball 266 and onto x-ray detector 254. Commonly-owned U.S. Pat. No. 6,928,140 teaches a method of inspecting a golf ball using x-ray radiation and metal markers abutting the surface of said golf ball is incorporated herein by reference in its entirety. Preferably, x-ray generating apparatus 250 emits radiation at an intensity that allows the core and the edges of the core of golf ball 266 to be clearly distinguished in the resultant image. Subsequent to passing through golf ball 266, x-ray radiation passes onto scintillating plate 258 which produces an image in the visible electromagnetic range; said visible radiation then passes to image intensifier 264, composed of a number of photo-multiplier tubes, and is finally projected onto screen 268. The image displayed on screen 268 is photographed by digital photosensor 270. Golf ball 266 is then positioned in front of and photographed by digital photosensor 252. The images of golf ball 266 in the x-ray and visible electromagnetic ranges produced by detector 236 may be overlaid and studied at an analyzer to determine such characteristics as concentricity and eccentricity, as discussed in the '140 patent. Preferably, the visible range image can be used to show clearly and precisely the outer edge of the cover of golf ball 266, while the x-ray image may show the position of the core of golf ball 266. By measuring the distance between the edge of the core and the edge of the cover of golf ball 266 at various points along the surface of the ball, the concentricity of the ball can be determined. The x-ray image may also be used in conjunction with the visible image to show contaminants in the core and intermediate layers of golf ball 266. Contaminants will generally appear more opaque in the x-ray image then the core and intermediate layer material. By overlaying the x-ray image with the visible image, the position of the contaminants relative to the outer cover of the ball may be determined.

In yet another example of the above-described embodiment, a detector of the inspection system of the present invention produces at least two x-ray images of a golf ball, a first image produced using low-energy x-ray radiation and a second image produced using high-energy x-radiation. The first image is preferably produced using radiation having an intensity that allows the cover to be clearly viewed, while the second image is preferably produced using radiation having a greater intensity that allows the core and the edge of the core to be clearly seen. Similar to example above, when the images are overlaid characteristics of the core and intermediate layers, such as eccentricity, concentricity and the presence of contaminants, may be determined relative to the outer cover. In accordance with this aspect of the invention, more than two intensities of x-ray radiation may be utilized to produce images of the golf ball under inspection.

Figure 5:
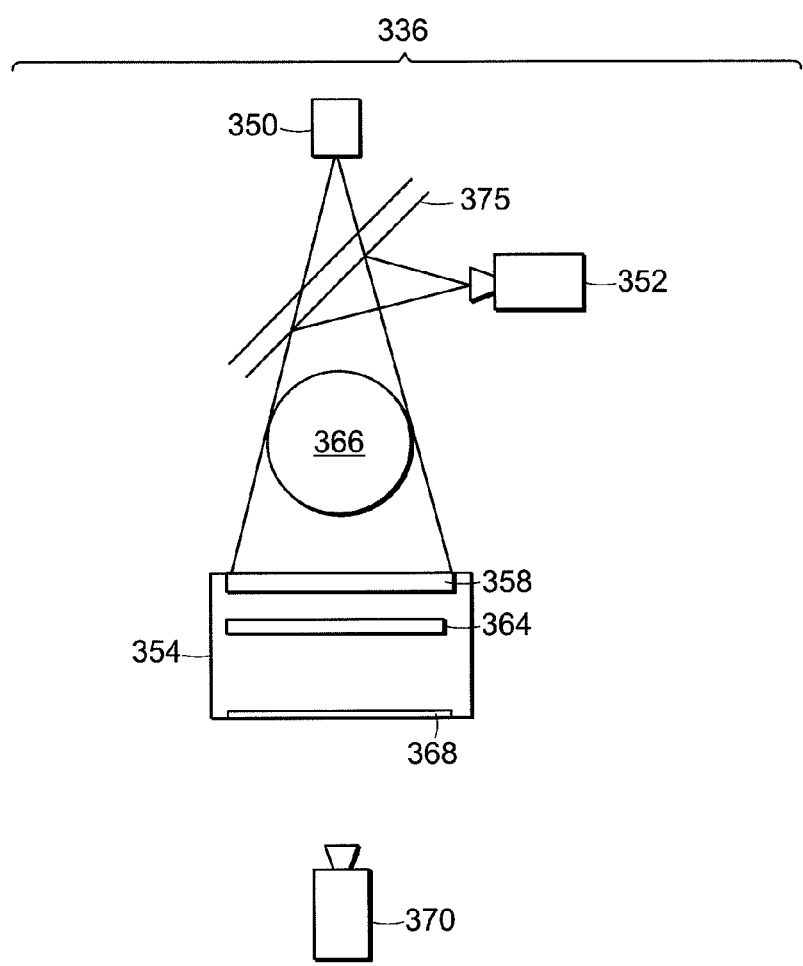
FIG. 5 is a schematic diagram of detector 336 configured to produce images in both the visible and x-ray range.

In another example of the above-described embodiment, an x-ray image and a visible-light image are captured simultaneously. An inspection system comprises an analyzer having a vision engine, a monitor and a keyboard, connected via an electronic link to detector 336, which is shown in detail in FIG. 5. Mirror 375 is transparent to x-ray radiation but reflective of visible light and is positioned between x-ray generating apparatus 350 and golf ball 366. Preferably, mirror 375 is made from aluminum. X-ray radiation is emitted by x-ray generating apparatus 350 through mirror 375 and golf ball 366 and onto x-ray detector 354. As in the above-described example, scintillator 358 converts the x-ray radiation into visible light. The image in the visible electromagnetic range is enhanced by image intensifier 364, composed of a number of photo-multiplier tubes, and is then projected onto screen 368. A first digital photosensor 370 then takes a picture of the image on screen 368. With golf ball 366 still in the same position, a second digital photosensor 352 captures the image in the visible electromagnetic spectrum of golf ball 366 reflected by mirror 375. The visible and x-ray images can be captured simultaneously. The images can be consulted to determine surface and subsurface characteristics of the object under inspection, and because the object under inspection does not need to be moved or repositioned after a first photosensor has collected an image in order for the second photosensor to collect an image, the object under inspection can be aligned identically in both images. In accordance with this aspect of the invention, the respective images of digital photosensor 370 and digital photosensor 352 may be aligned with alignment software using a calibration grid visible in both images, for instance a grid composed of steel or lead wire.

Alternatively, digital photosensor 370 and digital photosensor 352 can be replaced with digital video cameras. Each frame of video of the visible range image correlates to one frame of video of the x-ray range image, providing a moving image of the object under inspection showing both the surface of sub-surface details of the object.

While the above-described embodiments refer to the inspection of golf balls, the detection systems described can be used to capture images of any object. Specifically, the systems designed to capture images in both the visible and non-visible electromagnetic range can be utilized in the field of medical imaging. The detection apparatuses shown in FIGS. 2, 4 and 5, for example, can be used to capture visible and x-ray images of human body parts. The detection apparatus of FIG. 5 can be of particular utility in medical imaging as the body part being examined does not need to be moved or repositioned to capture images in the x-ray and visible ranges. A combination of visible and x-ray images of a body part can allow a medical professional or technician to view sub-surface elements, such as bones, in relation to the outer boundary of the body part. In addition, the visible range image can show the details of elements that are not captured in x-ray images, such as the skin or other soft tissue. Medical professionals and technician can refer to the visible range image separately or overlaid/blended with an x-ray range image to discern the condition of the body part being examined. Alternatively, multiple x-ray images of a body part may be taken, each x-ray varying with respect to wavelength. For instance, images of a body part may be collected using high and low-energy x-rays. The various images may then be overlaid or blended using imaging software to produce one image showing parts of the scene (or body part) captured by each of the separate images.

Yet another embodiment of the present invention includes utilizing high dynamic range video for surveillance purposes. In accordance with an aspect of the present invention, an imaging system is comprised of at least two photosensitive pixel arrays, similar to the multi-photosensitive pixel array camera discussed in previous embodiments. For each frame of video collected by a camera of the present invention, light is directed, through use of a beam-splitter or number of half-silvered mirrors, to at least two CCD or CMOS photosensor arrays. At least one array is overlaid with a neutral density filter. If two or more filters are being used, each neutral density filter is light-transparent to a different degree. Areas of the scene with intense luminance are captured in detail by an array coupled to the least light-transparent neutral density filter. Areas of moderate luminance are captured in detail by an array coupled to a moderately light-transparent neutral density filter. Dark or shadowed areas of the scene are shown in detail in the image of an array that stands alone or is coupled to a very light-transparent neutral density filter. Each frame of video is then comprised of three monochrome images, each image having a different exposure value. When digitally combined, each frame of video has a high light dynamic range. The resulting video images offer improved detail detection, which can be useful when utilized in security cameras or video surveillance equipment. A possible application of high dynamic range video surveillance is that each frame would show sharp features of an object, such as the face of a person, to assist in identification.

In a final embodiment of the present invention, an imaging system comprises two digital video image sensors, each image sensor configured to collect images in a different range of the electromagnetic spectrum. In one example, an imaging system comprises a digital video image sensor in the visible range and a digital video image sensor in the infrared range. Each frame of video in the visible range correlates to a frame of video in the infrared range, providing moving images of the scene under inspection. The imaging system of the present embodiment is particularly useful for surveillance purposes. In a scene with little incident visible light, e.g. an outdoor scene at night, the visible range video image sensor may not be capable of capturing objects in the scene in detail, however the infrared range video image sensor will pick up objects radiating the appropriate energy, e.g. a human radiating body heat. In scenes with a moderate or high amount of incident light, the images produced by the visible range video image sensor can provide visual detail, for instance the facial features of a person. According to this aspect of the invention, an infrared image sensor can be in the near, mid, or far infrared range. The visible range video image sensor can utilize a high dynamic range digital photosensor or a conventional low dynamic range digital photosensor.

In another example of the present embodiment, an imaging system comprises a first digital video image sensor capable of collecting small amounts of incident visible light and radiation in the lower-infrared range and processing the energy in an image-intensifier tube, and a second digital video image sensor capable of capturing images in the infrared range. The first image sensor, commonly referred to as a night-vision device, can produce images that offer visual detail of objects or persons in the scene, while the second image sensor can offer detail regarding the infrared energy being emitted by persons or objects in the scene. Alternatively, digital video image sensors of the present embodiment can be configured to collect many combinations of visible and non-visible range video images, such as visible and x-ray, near infrared and far infrared, infrared and ultraviolet, etc.

While it is apparent that the illustrative embodiments of the invention disclosed herein fulfill the objectives stated above, it is appreciated that numerous modifications and other embodiments may be devised by those skilled in the art. Therefore, it will be understood that the appended claims are intended to cover all such modifications and embodiments, which would come within the spirit and scope of the present invention.

We claim:

1. A method for automatically inspecting a golf ball, said method comprising the steps of:
   (i) producing at least two images of said first golf ball having different optical properties using an imaging system having at least two image sensors, wherein said image sensors produce at least two separate images in the same spectral range of the electromagnetic spectrum from the same perspective using a common light source to provide incident light for each image, said images being produced at different times in succession and wherein each image is of different brightness so that each image shows the same surface of the golf ball, each image having a different light exposure time so that different levels of incident light are captured and each image shows different visible areas and shadowed areas of the surface;
   combining said images from step (i) into one image, the single combined image showing the same surface of the golf ball as shown in the separate images, the different areas of the surface being equally visible on the combined image; and
   (iii) comparing the combined image to master images of an exemplary golf ball using an analyzer coupled to said imaging system via an electronic link so that defects on the surface of the first golf ball are detected.

2. The method of claim 1, wherein said analyzer employs an algorithmic image combining process to blend the tonal and luminance attributes of said images.

3. The method of claim 1, wherein said analyzer further comprises:
   (i) a vision engine to perform analytical operations on said images;
   (ii) a monitor to display images processed at said vision engine; and
   (iii) a keyboard.

4. The automated inspection system method of claim 3, wherein said image sensors are photosensitive pixel array image sensors arranged to collect at least two images of said golf ball in the visible electromagnetic range.

5. The method of claim 4, wherein each image sensor
   (i) is a charged-coupled device (CCD),
   (ii) is a complementary metal-oxide-semiconductor (CMOS) sensor,
   (iii) has a high electrical dynamic range,
   (iv) has a bit depth of 10 bits per pixel, or
   (v) has a bit depth of 12 bits per pixel.

6. The method of claim 5, wherein said images have varying light exposure values.

7. The method of claim 6, wherein said vision engine combines said images through an algorithmic process to produce one image with a high light dynamic range.

8. The of claim 7, wherein the image produced by the vision engine has a light dynamic range of 1000:1 to 2000:1.

9. The method of claim 7, wherein the image produced by the vision engine has a light dynamic range of 2000:1 to 4000:1.

10. The method of claim 7, wherein the image produced by the vision engine has a light dynamic range of greater than 4000:1.

11. The automated inspection system method of claim 3, wherein said monitor is a high dynamic range display device.

12. The automated inspection system method of claim 7, wherein said vision engine utilizes a tone-mapping technique to convert the tonal values of said combined image.

13. The automated inspection system method of claim 7, further comprising a light meter to measure luminance values of a scene containing said golf ball.

14. The method of claim 4, wherein a camera includes the at least two photosensitive pixel array image sensors and wherein the array of pixels of each image sensor absorbs light to a different degree.

15. The method of claim 14, wherein said vision engine employs an algorithmic image combining process to blend the images produced by each of the image sensors into one image having high light dynamic range.

16. The method of claim 15, wherein said camera includes three photosensitive pixel array image sensors.

17. The method of claim 15, wherein each image sensor is a charged-coupled device (CCD) or a complementary metal-oxide-semiconductor (CMOS) sensor.

18. The method of claim 15, wherein said camera further comprises a beam splitter to direct photons to each of the image sensors.

19. The automated inspection system method of claim 15, wherein said camera includes a number of half-silvered mirrors to direct photons to each of the image sensors.

* * * * *